United States Patent
Clayton et al.

(10) Patent No.: US 8,758,436 B2
(45) Date of Patent: Jun. 24, 2014

(54) EAR INSERT FOR RELIEF OF TMJ DISCOMFORT AND HEADACHES

(76) Inventors: Lawrence G. Clayton, Rockford, IL (US); William Coole, Belvidere, IL (US)

(*) Notice: Subject to any disclaimer, the term of this patent is extended or adjusted under 35 U.S.C. 154(b) by 527 days.

(21) Appl. No.: 12/561,464

(22) Filed: Sep. 17, 2009

(65) Prior Publication Data
US 2011/0066176 A1    Mar. 17, 2011

(51) Int. Cl.
*A61F 2/18* (2006.01)
*A61F 11/00* (2006.01)
*A61F 11/08* (2006.01)

(52) U.S. Cl.
CPC .............. *A61F 11/00* (2013.01); *A61F 11/002* (2013.01); *A61F 2/18* (2013.01); *A61F 11/08* (2013.01); *A61F 2230/0069* (2013.01); *A61F 2210/0014* (2013.01)
USPC .......................................... 623/10

(58) Field of Classification Search
USPC ............... 623/10, 23.7, 1.44–1.45, 1.18–1.2, 623/1.32–1.33; 606/108–109, 198, 199; 604/385.17–385.31; 128/864; 381/328
See application file for complete search history.

(56) References Cited

U.S. PATENT DOCUMENTS

| | | | |
|---|---|---|---|
| 2,230,738 A | 2/1941 | Baum | |
| 3,811,437 A * | 5/1974 | Gardner, Jr. | 128/864 |
| RE29,487 E * | 12/1977 | Gardner, Jr. | 128/864 |
| 4,094,303 A | 6/1978 | Johnston | |
| 4,776,322 A | 10/1988 | Hough et al. | |
| 5,203,352 A | 4/1993 | Gardner, Jr. | |
| 5,381,484 A | 1/1995 | Claes et al. | |
| 5,395,168 A | 3/1995 | Leenen | |
| 5,480,433 A | 1/1996 | Nadol, Jr. | |
| 5,553,152 A | 9/1996 | Newton | |
| 5,573,015 A | 11/1996 | Williams | |
| 5,645,584 A | 7/1997 | Suyama | |
| 5,717,771 A | 2/1998 | Sauer et al. | |
| 5,769,891 A | 6/1998 | Clayton | |
| 6,055,319 A | 4/2000 | Shennib et al. | |
| 6,122,388 A | 9/2000 | Feldman | |
| 6,123,722 A * | 9/2000 | Fogarty et al. | 623/1.1 |
| 6,337,915 B1 | 1/2002 | Lewis | |
| 7,536,023 B2 | 5/2009 | Leedom et al. | |
| 2006/0098833 A1 | 5/2006 | Juneau et al. | |
| 2007/0183613 A1 | 8/2007 | Juneau et al. | |
| 2009/0228103 A1 | 9/2009 | Clayton | |

OTHER PUBLICATIONS

Wikipedia. "Ear canal". Wikipedia, the free encyclopedia. Downloaded from <http://en.wikipedia.org/wiki/Ear_canal> on Oct. 1, 2012.*
U.S. Patent & Trademark Office, International Search Report in International Patent Application No. PCT/US2008/077339 (Nov. 26, 2008).
U.S. Patent & Trademark Office, Written Opinion in International Patent Application No. PCT/US2008/077339 (Nov. 26, 2008).
U.S. Patent & Trademark Office, International Preliminary Report on Patentability in International Patent Application No. PCT/US2008/077339 (May 6, 2011).

* cited by examiner

*Primary Examiner* — Andrew Iwamaye
(74) *Attorney, Agent, or Firm* — Oakland Law Group PLLC

(57) ABSTRACT

An expansible ear canal insert for treating TMJ disorders and headaches which acts directly on the TMJ and associated ligament and muscle structures to reduce stress and loads placed on the articulator disc located between the temporal bone and the mandible, as well as supportive muscles and ligaments near the TMJ. The insert is adapted to expand by application of body heat. In the expanded condition, the insert provides support to the TMJ and associated ligament and muscle structures.

9 Claims, 4 Drawing Sheets

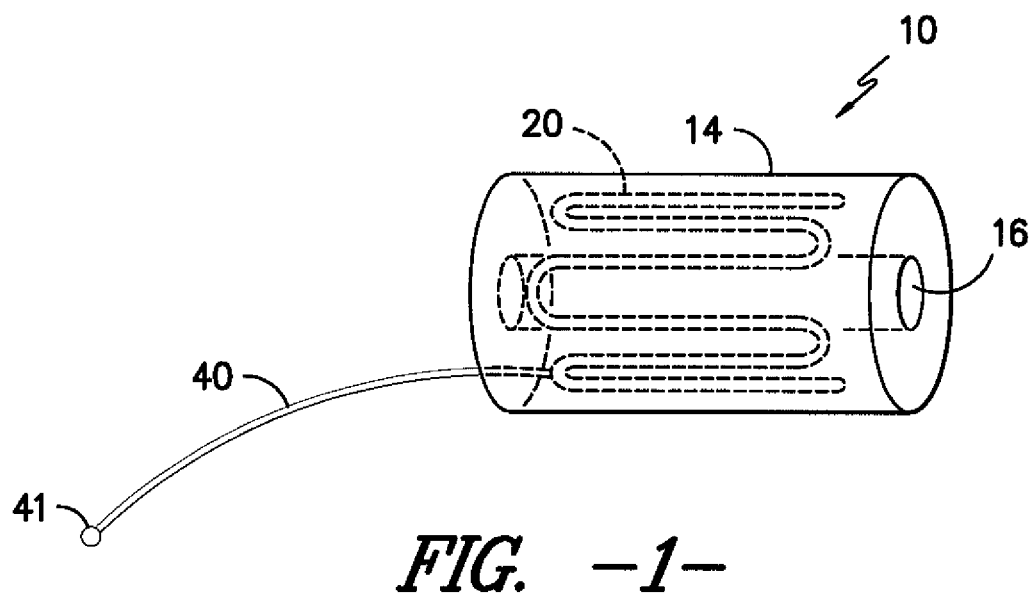
FIG. -1-
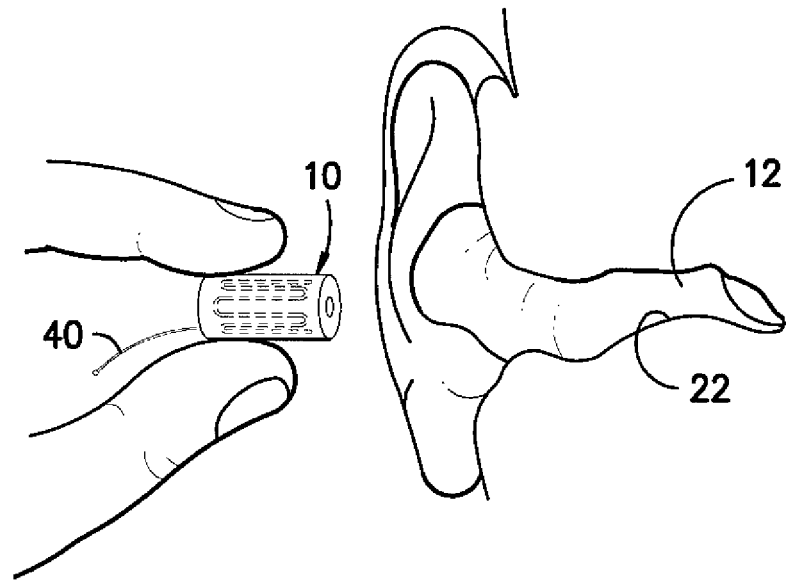
FIG. -2-

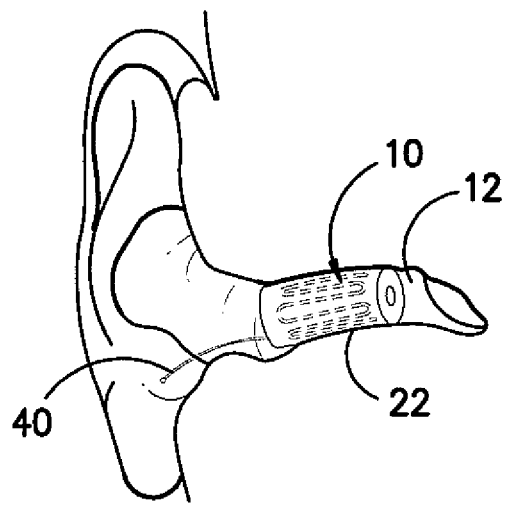
FIG. -3-
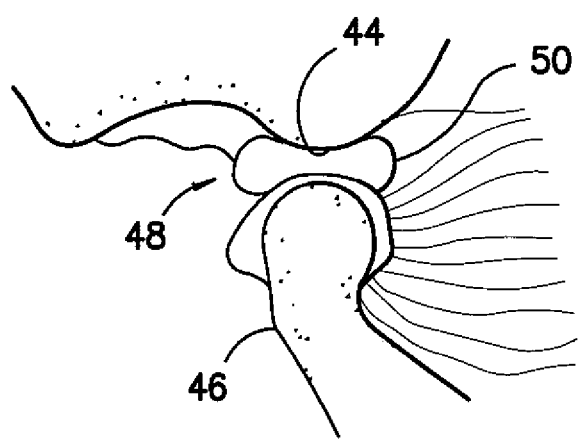
FIG. -4-

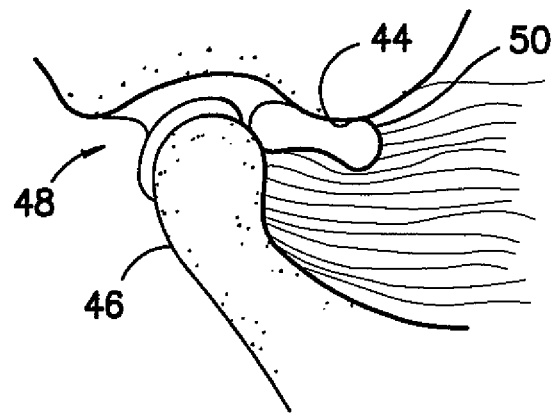
FIG. -5-
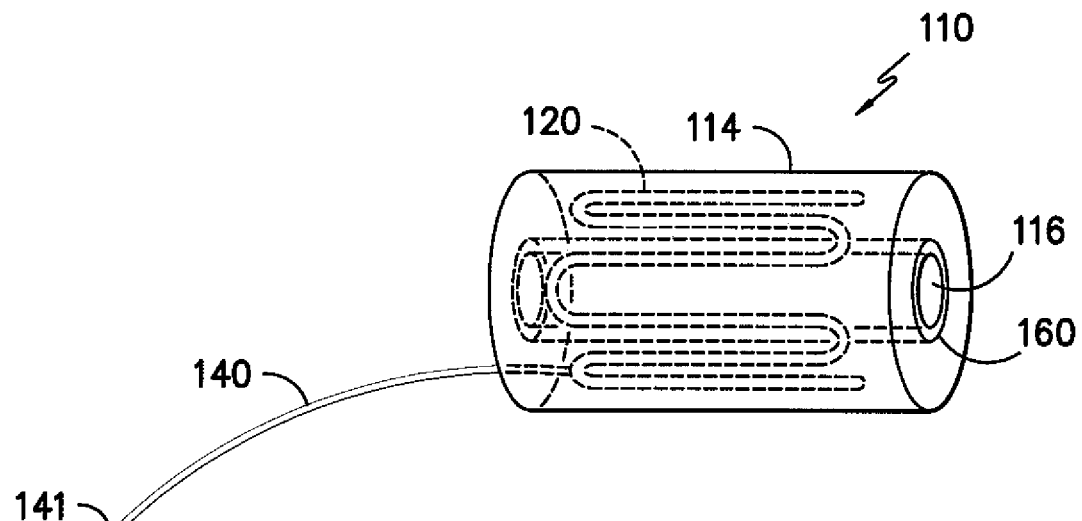
FIG. -6-

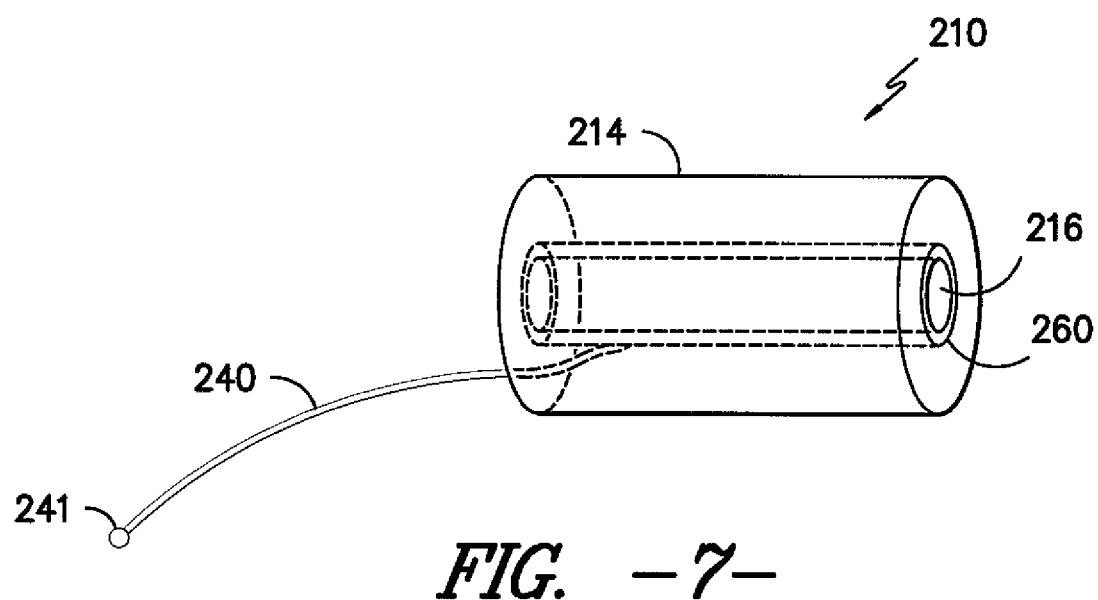
FIG. -7-

EAR INSERT FOR RELIEF OF TMJ DISCOMFORT AND HEADACHES

TECHNICAL FIELD

The present disclosure relates generally to medical devices, and more particularly, to medical devices for alleviation of jaw discomfort and/or headaches.

BACKGROUND

Many people suffer from pain in the joint located between the skull and the jaw. The joint is formed between the temporal bone of the skull and the mandible or jaw bone, and is commonly known as the temporo-mandibular joint or "TMJ". The human body has two temporo-mandibular joints, one located on each side of the jaw in front of each ear. The TMJs move every time a person chews, talks, or swallows.

In greater detail, the TMJ is a paired joint articulating the mandibular condyle, articulator disc, and squamous portion of the temporal bone. The TMJ is capable of both glide and hinge movements. Specifically, the TMJ is formed by the mandibular condyle fitting into the mandibular fossa of the temporal bone. A separation of these two bones is accomplished by the articulator disc which is composed of dense fibrous connective tissue. Ligaments attach the articulator disc to the condyle, permitting rotational movement of the articulator disc during mouth opening and closure.

Displacement of the articulator disc introduces strain to the jaw muscles and causes muscle pain or fatigue around the jaw. In addition, articulator disc displacement often causes a painful clicking in the TMJ during certain jaw movements as the disc moves between normal and displaced positions. A number of other symptoms may occur as a result of a strained disc, including TMJ lock, shoulder, neck, and back pain, and headaches.

Conventional methods of treating temporo-mandibular joint disorders can be costly, physically cumbersome, involve invasive and irreversible treatment or be time consuming. Some conservative methods for treating TMJ discomfort include the use of an intra-oral splint, medication, and life style changes. One type of intra-oral splint is a stabilization apparatus which is used to help alter the posture of the mandible to a more open, relaxed, resting position. Another type of intra-oral splint is an anterior positioning apparatus. The anterior positioning apparatus attempts to decrease the compression load on the joint and alter the structural condyle disc relation. Both types of splints, however, cannot be used full time without risking displacement of teeth. Treatment by medication often involves the use of addictive drugs and/or anti-depressants and therefore can lead to misuse and abuse. In addition, medications often produce adverse side effects in the patient. Other conservative methods include chiropractic or physical therapy. Unfortunately, these methods require extensive time commitments and physical exertion by the patient.

More aggressive treatment of TMJ discomfort includes orthodontic treatment such as grinding down of teeth and various types of surgery. Orthodontic treatments, however, merely indirectly address TMJ pain by adjusting the dental articulation and overall bite of the patient. Furthermore, orthodontic approaches are invasive, irreversible, and expensive.

An alternative procedure and related apparatus for treatment of TMJ discomfort are disclosed in U.S. Pat. No. 5,769,891, the contents of which are incorporated by reference herein in their entirety. According to the disclosure in U.S. Pat. No. 5,769,891, a prosthesis is provided for insertion into the ear canal. The prosthesis has a rigid structural portion of a shape conforming to the ear canal when the jaw is in an open position. The prosthesis provides added support to the TMJ and associated secondary musculature to reduce strain in the TMJ area. In practice, this prosthesis is inserted into the ear canal with the jaw in either the open or closed position. Support is provided when the jaw is closed as the internal diameter of the ear canal is reduced. Another apparatus for treatment of TMJ discomfort is disclosed in U.S. patent application Ser. No. 12/075,046 (incorporated by reference). This apparatus likewise uses a substantially rigid structure providing support to the TMJ and associated secondary musculature.

Many people also suffer from severe headaches. In some instances, such headaches are related to defined TMJ disorders. In other cases, the headaches are not related to any discernable TMJ disorder. It has been found that the insertion of a substantially rigid prosthesis as disclosed in U.S. Pat. No. 5,769,891 and U.S. patent application Ser. No. 12/075,046 may provide relief for a sizeable percentage of people who suffer from headaches even where there is no discernable TMJ disorder. Without being limited to a specific theory, the present inventors believe that that support within the ear canal may reduce tension in surrounding muscles and ligaments, thereby relieving stress that may cause a tension headache.

While the prior rigid devices are believed to provide substantial benefits, they have to be sized for individual users or classes of users. Thus, a structure that is substantially self-adjusting for users of different sizes would be desirable.

SUMMARY OF THE DISCLOSURE

According to one aspect, the present disclosure provides an ear canal insert for treating TMJ disorders and/or headaches which acts directly on the TMJ and associated ligament and muscle structures to reduce stress and loads placed on the articulator disc located between the temporal bone and the mandible, as well as supportive muscles and ligaments near the TMJ. The insert includes an internal support and a deformable covering adapted to conform to the contours of the ear canal when the internal support and/or the deformable covering is expanded. In the expanded condition, the insert provides support to the TMJ and associated ligament and muscle structures. This support maintains the ear canal in an expanded circumferential condition generally approximating the ear canal when the jaw is open.

According to another aspect, the present invention provides an ear canal insert for treating TMJ disorders. The insert includes a deformable, covering of heat expansible material. The covering expands when exposed to body heat to conform to the contours of the ear canal. In the expanded condition, the insert provides support to the TMJ and associated ligament and muscle structures.

These and other aspects of the disclosure will become more apparent from the following detailed description when taken in conjunction with the accompanying drawings.

BRIEF DESCRIPTION OF THE DRAWINGS

FIG. 1 is a cut-away view illustrating an exemplary insert for insertion into an ear canal for treatment of TMJ discomfort incorporating an expansible endoskeleton frame disposed in embedded relation within a deformable cover;

FIG. 2 is a view illustrating insertion of the exemplary insert of FIG. 1 into the ear canal of a user;

FIG. 3 is a view similar to FIG. 2 showing the exemplary insert in the ear canal with the endoskeleton frame in expanded condition;

FIG. 4 is a side view of a TMJ in an unoccluded condition with the disc in the normal position;

FIG. 5 is a side view of a TMJ showing the disc in a displaced orientation;

FIG. 6 is a cut-away view illustrating another embodiment of an insert for insertion into an ear canal for treatment of TMJ discomfort incorporating an expansible endoskeleton frame disposed within a deformable cover with a solid wall hollow sound bore at the interior of the endoskeleton frame; and FIG. 7 is a view similar to FIG. 6 illustrating another embodiment of an insert for insertion into an ear canal for treatment of TMJ discomfort incorporating an expansible cover with a solid wall hollow sound bore at the interior.

While the concepts of the instant disclosure are susceptible to various modifications and alternative constructions, certain illustrative embodiments thereof have been shown in the drawings and will be described below in detail. It should be understood, however, that there is no intention to limit the invention to the specific forms disclosed, but on the contrary, the intention is to cover all modifications, alternative constructions and equivalents falling within the spirit and scope of the disclosure as defined by the appended claims and all equivalents thereto.

DETAILED DESCRIPTION OF EXEMPLARY EMBODIMENTS

Exemplary constructions and practices will now be described through reference to the drawings, wherein like elements are designated by like reference numerals in the various views. For purposes of illustration, FIG. 1 illustrates a prosthesis 10 adapted for insertion into an ear canal 12 as shown generally at FIGS. 2 and 3. According to a contemplated practice, the prosthesis 10 includes a hollow deformable body 14 incorporating an interior sound transmission channel 16 extending in tunnel-like relation along the length of the prosthesis.

In the illustrated exemplary construction the deformable body 14 has a generally sleeve-like configuration surrounding the sound transmission channel 16. According to one contemplated arrangement, the deformable body 14 is formed from silicone rubber or the like although other shape-conforming materials may likewise be used if desired. As shown, in the exemplary construction an endoskeleton frame 20 is disposed in embedded relation within the deformable body 14. The endoskeleton frame defines a support member within the deformable body 14. By way of example only, and not limitation, such a structure may be achieved by positioning the endoskeleton frame 20 about a mandrel corresponding generally to the size and shape of the desired sound transmission channel 16 and then casting the silicone rubber or other material forming the deformable body 14 around the mandrel and the endoskeleton frame 20. Once the silicone rubber or other material forming the deformable body 14 has cured, the formed sleeve structure with the embedded endoskeleton frame 20 can be pulled off of the shaping mandrel. This results in a hollow sleeve structure in which the endoskeleton frame 20 is embedded in the deformable body in surrounding relation to the open sound transmission channel 16.

According to one contemplated practice, the endoskeleton frame 20 is formed with an initial diameter which is compressible to assume a reduced size facilitating insertion into the ear canal 12. As will be described further hereinafter, it may be desirable to carry out the insertion into the ear canal with the user's mouth open due to the expanded condition of the ear canal. However, insertion may also take place with the user's mouth in a closed condition if desired. As illustrated, the endoskeleton frame 20 may utilize a generally serpentine ring structure disposed in surrounding relation to the sound transmission channel 16. As will be appreciated, such a structure may undergo substantial radial adjustment. However, it is likewise contemplated that any number of other configurations may be used if desired. By way of example only, and not limitation, various constructions for expansible endoskeletons are disclosed in US Patent Application 2007/0183613 in the name of Juneau et al. the teachings of which are incorporated herein by reference in their entirety.

In accordance with one contemplated practice, the endoskeleton frame 20 may be formed from a so called "shape memory alloy" such as a nickel titanium alloy or the like. Such materials may have a relatively malleable character at typical room temperatures and take on a substantially more rigid state upon being subjected to elevated temperature conditions such as exist in the human body. Accordingly, in practice the endoskeleton frame 20 may be compressed by a user prior to insertion into an ear canal and thereafter be allowed to expand back to a pre-deformed shape after insertion into the ear canal as it is exposed to body heat. Moreover, in the elevated temperature state, the endoskeleton frame of shape memory alloy is characterized by enhanced rigidity due to a martensitic solid phase transformation at such temperatures. As will be described further hereinafter, such enhanced rigidity provides a desirable level of support to the prosthesis 10 within the ear canal 12.

While the use of a shape memory alloy may be desirable in some circumstances, it is likewise contemplated that other materials may be used which remain rigid at room temperature, but which nonetheless exhibit expansion at body temperature conditions. By way of example only, and not limitation, it is contemplated that one material that may be used in forming the endoskeleton frame 20 is a manganese/copper/nickel alloy or the like characterized by a relatively high coefficient of thermal expansion. By way of example only, one such material that may be used is a 72% manganese, 18% copper, 10% nickel alloy sold under the trade designation High Expansion 72 by Carpenter Technology having a place of business in Reading Pa. However, other alloys with relatively high coefficients of thermal expansion at body temperature conditions may also be used.

It is also contemplated that naturally resilient materials which are readily compressible but which bias outwardly in a spring-like manner following compression may be used in forming the endoskeleton frame 20. By way of example only, and not limitation, resilient polymers such as nylon and the like which are suitable for machining or other formation practices to provide a serpentine ring structure or other structure as may be desired may be particularly desirable.

While the use of an expandable endoskeleton frame 20 with a resilient covering may be desirable for many applications, it is likewise contemplated that the covering itself may be substantially expandable upon application to body heat. This expansion may be in conjunction with corresponding expansion of an internal endoskeleton. Alternatively, expansion of the resilient covering may be substantially independent of any internal endoskeleton. In fact, it is contemplated that the internal endoskeleton may be eliminated entirely in some instances.

By way of example only, and not limitation, it is contemplated that in one exemplary practice the deformable body 14 may be formed from an open cell foam such as a polyurethane foam or the like which has been loaded with plastic microspheres or other expansible fillers adapted to expand and contract in a substantially reversible manner upon application and removal of heat. When such an insert is inserted into the ear canal 12, the expansible fillers expand thereby causing the foam to expand and take on a more rigid character. Upon removal from the ear canal 12, the microspheres then contract back to the original state. As will be described further hereinafter, in the expanded state, the prosthesis will hold the ear canal in an open condition thereby providing support to the adjacent muscles and ligaments associated with the proximate temporo-mandibular joint It is also contemplated that the deformable body 14 may be formed from a foam material or the like characterized by a relatively high coefficient of thermal expansion at body temperatures such that the use of expansible fillers is not required. In this regard, body temperature sensitive foams or other materials which expand and take on enhanced rigidity may be particularly useful.

Regardless of the specific configuration of the prosthesis that may be used, the prosthesis operates by expanding within the ear canal so as to hold the ear canal in an open condition similar to the condition the ear canal has with the mouth in an open condition prior to insertion. This support within the ear canal provides corresponding support to the proximately positioned TMJ. FIG. 2 illustrates the insertion of a compressed prosthesis 10 into the ear canal 12 by a user. FIG. 3 illustrates the prosthesis 10 within the ear canal after insertion with the deformable body 14 expanded at least partially back to its pre-deformed state as a result of exposure to body heat and/or due to natural resiliency. As will be appreciated, the expansion of the deformable body 14 causes the deformable body 14 to press outwardly into generally conforming relation relative to the walls of the ear canal 12. In this state, the prosthesis 10 acts to hold the ear canal open.

According to a potentially desirable practice, the length of the deformable body 14 is selected such that a distal end portion extends slightly past the bend in the ear canal known as the isthmus 22. The isthmus 22 is in close proximity to the temporo-mandibular joint and is located approximately 20-22 millimeters from the outside of an adult ear. However, this distance may vary in different individuals. It is contemplated that using a deformable body having a length such that it extends substantially from the entrance to the ear canal into engagement with the isthmus facilitates providing desired support to the proximately positioned temporo-mandibular joint.

As illustrated, it is contemplated that at least one anterior projecting retraction element 40 may extend away from the deformable body 14 so as to project towards the exterior of the ear. Following insertion, at least a portion of the retraction element 40 may reside outside of the ear canal 12. In this position, a wearer may grasp the retraction element 40 to facilitate removal of the prosthesis 10.

The retraction element 40 is preferably substantially pliable to facilitate insertion and aid in removability while avoiding discomfort to the wearer. At the same time, the retraction element 40 should be characterized by sufficient strength to avoid breakage. By way of example only, and not limitation, it is contemplated that a suitable retraction element 40 may be formed from thermoplastic monofilament nylon adhesively bonded onto a surface of the endoskeleton frame 20 or a surface of the deformable body 14. However, other suitable polymeric or non-polymeric materials may likewise be utilized if desired. The retraction element 40 may include a bulbous head portion 41. Such a bulbous head portion 41 may enhance the ability of a wearer to grasp the retraction element 40 during removal of the prosthesis 10 from the ear canal 12. In the event that the retraction element 40 is formed from nylon or other thermoplastic material, a suitable bulbous head portion 41 may be formed by selectively melting the terminal end of the retraction element 40 to form a melted polymer bead which is thereafter permitted to resolidify. The surface of the resolidified bead may thereafter be smoothed by sanding or other suitable treatment to remove irregularities so as to enhance comfort during use.

Referring now to FIGS. 4 and 5, in the expanded condition the prosthesis 10 influences the relationship between the temporal bone 44 and the mandible 46 in each temporo-mandibular joint 48, thereby relieving pain inducing stress in the temporo-mandibular joint 48 and related muscles, ligaments, and nerves. In this regard, it will be appreciated that one source of temporo-mandibular joint discomfort is a dislocated articulator disc 50. As shown in FIG. 4, when the jaw or mandible 46 is in an open or unoccluded position corresponding to the mouth being open, the articulator disc 50 is usually in a normal, unstrained position between the temporal bone 44 and a condyle surface of the mandible 46. As is often the case with a person experiencing temporo-mandibular joint discomfort, the articulator disc 50 slips to a displaced position when the mandible 46 is subsequently closed, as illustrated in FIG. 5. The displacement of the articulator disc 50 is often indicated by a clicking or popping noise as the mandible 46 moves between open and closed positions. In the displaced position, the articulator disc 50 is no longer between the condyle surface and the temporal bone 44, and the articulator disc 50 and attached ligaments become strained. Strain on these members stresses the surrounding muscles, which may ultimately result in face, neck, and back pain.

To treat temporo-mandibular joint discomfort arising from a displaced articulator disc 50, the prosthesis 10 is provided for reducing stresses and loads on the articulator disc 50. The prosthesis 10 reshapes and holds the ear canal in a condition substantially corresponding to the condition when the mouth is open thereby providing a support structure which helps align the temporo-mandibular joint 48 and associated muscles and ligament structures so that the temporo-mandibular joint 48 has a normal rotational movement. Strain or compression on the articulator disc 50 is therefore reduced, thereby alleviating pain in the temporo-mandibular joint and associated structures. It may be desirable for the user's mouth to be held in an open condition during insertion of the prosthesis 10 such that the expandable prosthesis naturally conforms with the naturally occurring expanded condition the ear canal has when the mouth is open. However, the prosthesis 10 may also be inserted with the mouth in a closed position followed by expansion of the prosthesis causing the ear canal to open more fully.

It is to be understood a dislocated disc is only one cause of temporo-mandibular joint discomfort and that there are many other sources of such pain. Nerves, ligaments, and muscle groups (such as the masticatory musculature) are located proximal to the temporo-mandibular joint, and improper loading, strain, or alignment of these members provide potential sources of temporo-mandibular joint pain. Rather than being limited to disc dislocation situations, as outlined above, the prosthesis 10 addresses misalignment and stress in the temporo-mandibular joint and related structures by supporting these structures for normal rotational movement.

The prosthesis 10 alleviates temporo-mandibular joint discomfort by supporting the temporo-mandibular joint 48 and associated muscles, nerves, and ligaments for proper rotation of the mandible between open and closed positions. By inserting the prosthesis 10 into the ear canal, the prosthesis will thereafter expand to urge the walls of the ear canal outwardly to take on the shape when the mandible 46 is open and disc 50 is in the normal position. That is, the ear canal 12 is expanded and held open as if the mandible 46 is open. In the expanded condition the sound transmission channel 16 is also held in an open condition such that hearing is not impaired. Thus, a natural body orifice is used to reposition the mandible 46 without requiring surgery or other painful and invasive techniques.

As noted above, the example of a dislocated disc is merely illustrative of a temporo-mandibular joint condition addressed by the present device and is in no means meant to limit the scope of the present invention. Accordingly, it will be appreciated that the present device addresses stresses and misalignments in not only the disc but also any muscles, ligaments, and nerves associated with the temporo-mandibular joint. As noted previously, the reduction in strain to the muscles and ligament structures is also believed to be beneficial in reducing headaches.

As will be appreciated, in the embodiment of FIG. 1, the expansion of the endoskeleton 20 acts to hold the sound transmission channel 16 in an open condition by virtue of spreading radially outwardly. The endoskeleton 20 also provides resistance against compression within the ear canal. FIG. 6 illustrates an alternative embodiment wherein elements corresponding to those described previously are designated by like reference numerals within a 100 series. Specifically, in the embodiment of FIG. 6, the prosthesis 110 includes a substantially rigid hollow tube or sound bore 160 of a material such as acrylic or the like that extends along the length of the deformable body 114 at the interior of the endoskeleton frame 120. In this construction, the interior of the hollow sound bore 160 defines the sound transmission channel 116. The hollow sound bore 160 also provides an interior support for the endoskeleton frame to limit compression during insertion. The sound bore 160 may be contoured to conform generally with the curvatures of the ear canal. In this regard, shapes such as illustrated in U.S. Pat. No. 5,769,891 and U.S. patent application Ser. No. 12/075,046 may be particularly useful.

In use, the rigid hollow sound bore 160 may aid in inserting the prosthesis 110 into the ear canal. Specifically, the rigid hollow sound bore 160 defines an additional support member providing a degree of axial rigidity even when the deformable body is in a substantially flexible state. Further, the solid wall construction of the sound bore aids in maintaining the sound transmission channel 116 in an open condition at all times. Thus, there is no interference with hearing during the period prior to expansion.

The exemplary prosthesis 110 illustrated in FIG. 6 also includes at least one anterior projecting retraction element 140 including a bulbous head portion 141 extending away from the deformable body 114 so as to project towards the exterior of the ear as previously described. The retraction element 140 may be adhesively bonded onto a surface of the endoskeleton frame 120, a surface of the sound bore 160 or a surface of the deformable body 114.

FIG. 7 illustrates still another exemplary embodiment wherein elements corresponding to those described previously are designated by like reference numerals within a 200 series. In the embodiment of FIG. 7, the prosthesis 210 is devoid of an expanding endoskeleton frame. Rather, expansion is provided by the material forming the deformable body 214. As noted previously, such material may include shape conforming temperature sensitive foams and the like which expand upon exposure to body heat. Such expansion causes the deformable body 214 to press outwardly on the walls of the ear canal thereby holding the ear canal open in a condition corresponding to the condition of the ear canal when the jaw is open. As shown, the exemplary prosthesis 210 includes a support member in the form of a substantially tubular sound bore 260 of solid wall construction formed from a material such as acrylic or the like that extends along the length of the deformable body 214. In this construction, the interior of the hollow sound bore 260 defines the sound transmission channel 216.

In use, the rigid hollow sound bore 260 may aid in inserting the prosthesis 210 into the ear canal by providing a degree of axial rigidity even when the deformable body is in a substantially flexible state. Further, due to the solid wall construction of the sound bore, the sound transmission channel 216 remains open at all times. Thus, there is no interference with hearing once the deformable body 214 has expanded. The sound bore 260 may be contoured to conform generally with the curvatures of the ear canal. In this regard, shapes such as illustrated in U.S. Pat. No. 5,769,891 and U.S. patent application Ser. No. 12/075,046 may be particularly useful.

The exemplary prosthesis 210 also includes at least one anterior projecting retraction element 240 including a bulbous head portion 241 extending away from the deformable body 214 so as to project towards the exterior of the ear as previously described. The retraction element 240 may be adhesively bonded onto a surface of the sound bore 260 or a surface of the deformable body 214.

It will be appreciated that the foregoing description provides examples of the disclosed apparatus and method of use. However, it is contemplated that other implementations of the disclosure may differ in detail from the foregoing examples. All references to examples herein are intended to reference the particular example being discussed at that point and are not intended to imply any limitation as to the scope of the disclosure or claims more generally. All language of distinction and disparagement with respect to certain features is intended to indicate a lack of preference for those features, but not to exclude such from the scope of the claims entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by the context.

Accordingly, this disclosure contemplates the inclusion of all modifications and equivalents of the subject matter recited in the appended claims as permitted by applicable law. Moreover, any combination of the above-described elements in all possible variations thereof is contemplated unless otherwise indicated herein or otherwise clearly contradicted by the context.

What is claimed is:

1. A prosthesis adapted to be inserted into an ear canal for supporting a joint between a mandible and a corresponding temporal bone, the ear canal having an entrance and an isthmus located at a position remote from the entrance, the prosthesis comprising:

a cylindrical deformable body including a sound transmission channel extending the length of the deformable body and an outer wall defining an outer circumference of the deformable body, the sound transmission channel being exposed to view from the entrance of the ear canal when the deformable body is positioned within the ear canal, the deformable body comprising a body temperature sensitive foam made from a material that is adapted to reversibly expand and contract upon application and removal of body heat in the ear canal, a retraction element having a first end coupled to the prosthesis and an opposite free end, the first end being spaced apart from the sound transmission channel and the free end residing outside of the ear canal when the prosthesis is inserted into the ear canal, the retraction element configured to be grasped by a wearer to remove the prosthesis, and at least one expansible endoskeleton frame having a ring structure entirely embedded within the deformable body, the expansible endoskeleton frame being disposed radially outward from and coaxially around the sound transmission channel and radially inward from the outer wall, the deformable body having a length adapted to extend between the entrance and the isthmus of the ear canal, the body temperature sensitive foam being adapted to expand and take on enhanced rigidity in the ear canal upon application of body heat such that the deformable body conforms in pressing relation against the walls of the ear canal thereby holding open the ear canal and supporting the joint, the expansible endoskeleton frame defining an outer diameter when the expansible endoskeleton frame is expanded, and the outer diameter of the expansible endoskeleton frame being greater than an outer diameter of the retraction element.

2. The prosthesis as recited in claim 1, wherein said at least one expansible endoskeleton frame is adapted to expand upon application of body heat such that the expansible endoskeleton frame conforms in pressing relation against the walls of the ear canal.

3. The prosthesis as recited in claim 2, wherein the expansible endoskeleton frame has a serpentine ring structure.

4. The prosthesis as recited in claim 1, wherein the expansible endoskeleton frame is formed from a shape-memory alloy.

5. The prosthesis as recited in claim 1, further comprising a solid wall sound transmission bore.

6. The prosthesis as recited in claim 5, wherein the expansible endoskeleton frame is disposed about the sound transmission bore.

7. The prosthesis as recited in claim 6, wherein the endoskeleton frame is formed from a shape-memory alloy.

8. The prosthesis as recited in claim 6, wherein the expansible endoskeleton frame has a serpentine ring structure.

9. The prosthesis as recited in claim 1, wherein the body temperature sensitive foam includes a heat expansible filler adapted to expand upon exposure to body temperature.

* * * * *